United States Patent [19]

Sherwin et al.

[11] Patent Number: 4,721,811

[45] Date of Patent: Jan. 26, 1988

[54] SYNTHESIS OF ALIPHATIC POLYAMINES

[75] Inventors: Martin B. Sherwin, Potomac; Shu-Chieh P. Wang, Columbia; Stewart R. Montgomery, Ashton, all of Md.

[73] Assignee: W. R. Grace & Co., New York, N.Y.

[21] Appl. No.: 769,286

[22] Filed: Aug. 26, 1985

[51] Int. Cl.$^4$ ............................................. C07C 85/12
[52] U.S. Cl. ..................................... 564/491; 564/490
[58] Field of Search ................................. 564/491, 490

[56] References Cited

U.S. PATENT DOCUMENTS

| | | | |
|---|---|---|---|
| 3,418,375 | 12/1968 | Schmitt et al. | 564/491 |
| 3,565,957 | 2/1971 | Mirviss | 260/583 |
| 3,673,251 | 6/1972 | Frampton et al. | 260/563 D |
| 3,733,325 | 5/1978 | Yeakey | 260/268 |
| 4,235,821 | 11/1980 | Butte et al. | 564/491 |
| 4,375,003 | 2/1983 | Allain et al. | 564/492 |

FOREIGN PATENT DOCUMENTS 122479   6/1944   Australia ............................ 564/491

*Primary Examiner*—Charles F. Warren
*Assistant Examiner*—Elizabeth A. Hanley
*Attorney, Agent, or Firm*—Howard J. Troffkin

[57] ABSTRACT

An improved process for selectively forming aliphatic polyamines from aliphatic polynitriles having 2 to 3 atoms between cyano groups by reacting aliphatic polynitrile, with hydrogen in the presence of a primary or secondary amine, through a fixed bed reactor while continuously contacting the reactants with granular Raney cobalt packed therein.

25 Claims, No Drawings

SYNTHESIS OF ALIPHATIC POLYAMINES

BACKGROUND OF THE INVENTION

The present invention relates to an improved process for forming non-cyclic, aliphatic compounds having a multiplicity of primary amino groups and forming these compounds in high yields and selectivity from the corresponding polynitrile having from 2 to 3 atoms between the cyano groups.

The hydrogenation of nitriles to amines using conventional hydrogenation catalysts is well known. However, it is recognized that this synthetic mode is not an effective process for forming noncyclic, aliphatic compounds from polynitrile having an atomic structure capable of forming five and six membered ring containing compounds. In such cases the presently known hydrogenation processes provide noncyclic products in low selectivity and yield. This is especially true with polynitriles such as nitrilotriacetonitrile, iminodiacetonitrile and ethylenediaminetetraacetonitrile. Normally, the dominant products formed are cyclic polyamines. When one attempts to adjust the reaction conditions to those which may provide higher selectivity or yield of the non cyclic, aliphatic compound, one observes rapid inactivation of the catalyst materials used.

It is generally known that hydrogenation of nitriles can be accomplished by many modes such as by a batch process using an autoclave or by continuous process using a fixed bed reactor to contact a hydrogenation catalyst with a solution containing a nitrile. The reaction product is generally a mixture of primary, secondary and tertiary amines. The formation of the later two amines are thought to be due to the reaction of an imine intermediate with some of the primary amine product present in the reaction zone to produce a secondary amine, and in turn, the reaction of the imine with some of the secondary amine to form a tertiary amine product. When the starting nitrile has a multiplicity of cyano groups which are separated by an appropriate chain length of about 2 to 3 atoms, the secondary and tertiary amine formation tends to be intramolecular to provide cyclic compounds as the dominate product. Thus, when a dinitrile, such as iminodiacetonitrile, is subjected to conventional hydrogenation, one forms the cyclic compound, piperazine, as the major material. For a trinitrile, such as nitrilotriacetonitrile, the difficulty of forming the corresponding linear aliphatic amine, tris(2-aminoethyl) amine, increases geometrically. Thus, contacting of a polynitrile with a hydrogenation catalyst is a recognized route for producing cyclic polyamines.

U.S. Pat. Nos. 3,565,957 and 3,733,325 teach that the yields of the cyclic amine can be optimized by carrying out the reaction in the presence of large amounts of ammonia. By using a hydrogenation catalyst in the absence of ammonia to increase the yield of linear product, one produces a solid material which inactivates the catalyst in a very short period of time. The short life of the catalyst as well as low selectivity and yield has caused this process to be deemed economically unfeasible in commercially providing linear polyamines.

In all of the hydrogenation processes that are used in converting polynitriles to polyamines one requires using a solution of the initial polynitrile in an inert solvent. Materials which are known to be useful as inert solvents are alcohols, amides, and ethers as they do not interact with the other materials in the reaction zone to detract from the overall yield and selectivity of the products being formed. When the product desired is a cyclic amine, ammonia has, in certain instances, been utilized as a solvent or cosolvent for the process. It has been thought that due to the reactivity of the imine intermediate product with amine groups one should not utilize amine materials as the solvent in such processes as they would tend to interact with the imine to form a condensation reaction product and detract from the overall selectivity of the desired materials.

It is highly desired to find an economically feasible process for forming, in high selectivity and yield, non-cyclic aliphatic polyamines from corresponding polynitriles. The formed linear polyamines have known usefulness as chelating and sequestering agents and as reagents in the formation and crosslinking of polymeric products, such as polyurethanes and the like.

SUMMARY OF THE INVENTION

A continuous process for forming an aliphatic polyamine from a polynitrile selected from nitrilotriacetonitrile, iminodiacetonitrile and ethylenediaminetetraacetonitrile. The process provides aliphatic polyamines in high selectivity and high yields while not adversely affecting the catalyst activity or life. The process is thus an economical and technical advance over conventional processes.

The present process requires contacting of a polynitrile having its cyano groups separated by from 2 to 3 atoms, with granular Raney cobalt under a hydrogen pressure of from 500 to 10,000 psi in the presence of a primary or secondary amine which is introduced as part of the feed material. The process must be carried out in a fixed bed reactor having Raney cobalt as its packing and passing the reactants through the reaction zone in a manner to have a high ratio of Raney cobalt to polynitrile present, preferably in a trickle bed mode.

DETAILED DESCRIPTION OF THE INVENTION

The present invention is directed to a process which uses a combination of specific parameters to unexpectedly provide a means of forming aliphatic primary amines in high conversion and selectivity from polynitriles.

The process involves contacting, in a fixed bed reactor, a polynitrile and hydrogen with granular Raney cobalt. The polynitrile can be selected from compounds having at least two cyano groups separated by an immediate chain of 2 or 3 atoms. The cyano groups may be separated by hydrocarbon chains which are saturated or contain olefinic (ethylenic) unsaturation therein or may contain a heteroatom such as nitrogen, oxygen, sulfur, and the like or combinations thereof. Specifically, the most applicable polynitriles are nitrilotriacetonitrile, iminodiacetonitrile and ethylenediaminetetraacetonitrile as these materials provide highly desired noncyclic polyamines in an economical manner. Other polynitriles include oxidiacetonitrile, thiodiacetonitrile, 2-methylglutaronitrile and 1,3-dicyanopropene. These compounds are normally viewed as having the proper atom chain length to intramolecularly react and form stable cyclic compounds as the dominant product. However, the present process provides a means to cause the dominant product to be an aliphatic, non-cyclic polyamine.

The polynitrile reactant must be introduced into the reaction zone according to the present process in the presence of an organic primary or secondary amine moderating compound or mixtures thereof. In contrast to conventional processes where inorganic ammonia is introduced in large amounts to achieve high selectivity towards the cyclic amine product, one presently achieves high conversion and selectivity of the polynitrile to the non-cyclic, aliphatic amine product. It is also realized that conventional processes normally contain some primary amine compound as formed product in the reaction zone but these processes do not inhibit conversion of polynitrile to the cyclic product to provide the high yield (the product of conversion and selectivity) of the presently desired non-cyclic, aliphatic amine, as is presently achieved.

The amine moderator must be introduced as part of the liquid feed in conjunction with the polynitrile reactant. The amine may be contained in a liquid which is a co-solvent for both the polynitrile and the amine. Alternately, the amine may be used as the solvent for the polynitrile. The amine moderator should be introduced into the reaction zone in at least about 5 weight percent based on the weight of the polynitrile feed. It may be present in excess of the polynitrile and may be the solvent in which the nitrile is contained in concentrations, as described herein below. Any amine may be selected which contains at least one primary or secondary amino group, is capable of remaining liquid under reaction zone conditions, is mutually soluble with the other liquid feed material or is soluble in a cosolvent used to carry the feed materials into the reaction zone and is substantially free of other chemical moieties which may interact with the reactants or products in the reaction zone. Examples of suitable amines include monoamines such as butylamine, pentylamine, heptylamine and the like or polyamines, such as ethylenediamine, triethylenetetramine, tetraethylenepentamine and the like as well as mixtures thereof. Although it is not preferred, polyamines having four to six atoms between terminal amino groups may be used as part of the amine moderator. For example, one may wish to use a portion of the product amine of the present process as an amine moderator due to its ready availability and lack of requirement of added storage facilities. The preferred amine moderators are the polyamines with ethylenediamine being the most preferred as it is a strong solvent for the polynitrile reactants.

The polynitrile must be introduced into the reaction zone as a liquid and, therefore, is normally introduced as a solution in a solvent medium. As stated above, the amine moderator may act as the solvent for the polynitrile or it may be introduced as part of the polynitrile solution while using a cosolvent. Cosolvents suitable for this purpose include alcohols such as methanol, ethanol, isopropanol, n-butanol and the like; amides such as N,N-dimethylacetamide, formamide, N,N-dimethylformamide and the like; ethers such as dioxane and the like as well as other solvents which are inert to the reactants and the products in the reaction zone and are capable of remaining liquid under the reaction conditions. It is preferred that the polynitrile be introduced as a solution at concentrations of from 5 wt. percent to saturation, preferably from 5 to 30 wt. percent based on the total weight of the liquid solution introduced into the reaction zone.

It is understood that the specific polynitrile reactant chosen will determine the primary amine product to be formed. Each cyano group will be converted to a primary methyleneamine group. It has been found that when using the present process, the hydrogenation selectivity goes to the formation of primary amine product without any major interaction between the formed methyleneamine and the intermediate imine groups and especially substantially low intramolecular reaction.

The catalyst required to perform the present process is granular Raney cobalt. The catalyst is formed from an initial alloy which contains from about 50 to 70 wt. percent aluminum, from about 30 to 50 wt. percent cobalt, from 0 to about 6 wt.% chromium and from 0 to about 6 wt. percent molybdenum. Chromium and/or molybdenum may also be provided by treating the surface of an already activated alloy with a salt of these materials to provide from 0 to about 5 percent of these metals on the Raney cobalt surface. The most preferred catalyst is formed from alloys having small amounts (0.5 to 5 wt. percent) of chromium and/or molybdenum.

The catalyst is prepared by contacting the starting alloy with an aqueous alkaline solution formed from an alkali or alkaline earth metal hydroxide, preferably sodium hydroxide. The alloy should be granular, that is have a particle size of from about 0.02 to 0.5 inch and preferably from about 0.05 to 0.4 inch mean diameter. The activation is carried out in known manners by contacting the starting alloy with dilute, normally from about 1 to 10 wt. percent, preferably from 1 to 5 wt. percent, of an alkaline solution while maintaining a low temperature such as below about 50° C. and preferably below 40° C. Generally, it is best to activate the alloy at from about 20° to 40° C. Activation is readily monitored by the evolution of hydrogen and provides a suitable catalyst for use in the present process when from 20 to 40 percent of the aluminum is removed. The activated Raney cobalt catalyst is washed with water to free it from the alkaline solution and used immediately or stored under water or other inert atmosphere.

The process is carried out by using a fixed bed reactor packed with the above-described granular Raney cobalt catalyst through which the polynitrile reactant and primary amine moderator are passed. The polynitrile should be introduced into the packed reactor as part of the liquid feed at a flow rate of from about 0.02 to 10 and preferably from 0.05 to 2 grams of polynitrile/min-cm$^2$. Amine, polynitrile and, where applicable, solvent should be maintained in a liquid state in the reaction zone. The liquids should be introduced and flow concurrently through the reactor. Preferably, hydrogen gas is introduced and caused to pass through the reaction zone concurrently with the liquids. The granular and high surface area characteristics required of the catalyst, when combined with the relatively low flow rate discussed above, provides the required very high ratio of catalyst surface area to polynitrile reactant.

The contacting of the various materials in the reaction zone is most preferably done under trickle bed conditions in which the gaseous material is in a continuous phase while the liquid and solid materials therein are in a discontinuous phase. The term "trickle bed" used herein and in the appended claims refers to this 3-phase system and to velocities of the reactants flowing through the reaction zone which are capable of maintaining this 3-phase system with the gaseous material as the continuous phase. It is preferred that the liquid primary or secondary amine as well as any inert solvent used and the gaseous hydrogen be all permitted to flow concurrently with the polynitrile. Various descriptions have been made about this mode of contact including "Gas-Liquid-Solid Reactor Design" by Shah (1979); "Catalytic Reactor Design" by Tarhan (1983); and "Hydrodynamics and Solid-Liquid Contacting Effectiveness in Trickle-Bed Reactors", by Gianetto et al AIChE Journal, Vol. 24, No. 6 page 1087.

The polynitrile is contacted with the granular Raney cobalt catalyst in the presence of hydrogen and a liquid amine as described above. The hydrogen gas is introduced into the reaction zone at a rate sufficient to maintain a hydrogen pressure in the reaction zone of from 500 to 10,000 psi, preferably from 2,000 to 5,000 psi and most preferably from 2,500 to 4,000 psi. The amine moderator utilized in the present process must be introduced into the reactor as part of the liquid feed and permitted to flow concurrently with the polynitrile. The amine should be present in the reaction zone in at least 5% by weight based on the weight of the polynitrile and may be present in excess of the polynitrile including being the solvent media for the polynitrile.

The reaction zone should be maintained at an elevated temperature of from 50° to about 150° with from 70° to 120° C. being preferred. The pressure maintained in the reaction zone should be sufficient to maintain all of the reactants, the polynitrile, the primary or secondary amine monitor and the solvent in a liquid state as described above. The hydrogen pressure described above may be supplemented by partial pressure formed from an inert gas such as nitrogen.

The liquids are preferable introduced into the reaction zone along with the hydrogen gas in a manner to cause them to flow concurrently, preferably in downward direction. The hydrogen is introduced in a volume flow rate of from 100 to about 3,000, preferably from 300 to 2,000 standard cubic centimeter per minute-centimeter square (scc/min-cm$^2$) and a total liquid volumetric flow ranging from 0.1 to about 50 preferably from 0.2 to about 4 cc/min-cm$^2$. These rates have presently been found to provide sufficient flow of the polynitrile over the Raney cobalt catalyst to aid in providing a high catalyst to nitrile ratio. The residence time should be sufficient to produce an aliphatic polyamine as the dominant reaction product. A residence time of from about 2 to 10 minutes, preferably from 5 to 8 minutes is normally sufficient.

The following examples are given for illustratively purposes only and are not meant to be a limitation on the present invention except as defined by the claims appended hereto. All parts and percentages are by weight unless otherwise stated.

EXAMPLE 1

Hydrogenation of nitrilotriacetonitrile (NTAN) was carried out using a trickle bed tubular reactor fabricated from 316 stainless steel tubing of ⅜" inside diameter and about 36" long. The reactor was positioned vertically with an inlet feed tube located at its top for each of the feed materials to be supplied through high pressure pumps and the pressure controlled by a back pressure regulator. The reactor was packed granular Raney cobalt to provide a bed void fraction of about 0.3 and maintained at 100° C.

The granular Raney cobalt catalysts were prepared by treating granular alloys of aluminum, cobalt and chromium (60/38/2) of about 6 to 8 mesh (U.S. standard size) with dilute solutions of sodium hydroxide (about 5 wt. %) at a temperature of 35°±2° C. while monitoring the hydrogen gas evolution. The hydrogen gas evolution was used to measure the degree and extent of activation of the alloy. The activation was continued until about 30% of the original aluminum in the alloy was removed (based on 1.5 moles of hydrogen per mole of aluminum). The activated granules were washed with deionized water to a pH of 7.8 and then used immediately or stored under water.

NTAN was introduced at a liquid flow rate of 0.66 ml/min rate of 1 g/min into the tubular reactor as a 10 wt. % solution in ethylenediamine. Hydrogen was currently fed into the reactor with the NTAN at a rate of 220 scc/min. The reactor pressure was maintained at about 2,800 psi.

The reactor products were analyzed by gas-liquid chromotography and it was determined that there was 100 percent conversion of the polynitrile with molar selectivity to the desired linear tris(aminoethyl)amine (TREN) being 80% with only about 20% cyclic aminoethylpiperazine (AEP) formed. The catalyst exhibited good stability and extended activity.

EXAMPLE 2

For comparative purposes, the process described in Example 1 above was repeated except that the primary amino solvent, ethylenediamine, was replaced by using an equal amount of N,N-dimethylacetamide (DMAC). The material was again analyzed in the same manner using gas-liquid chromatography. It was determined that conversion was only about 80% and the selectivity of the products was down to about 60% for the linear product. In addition, the catalyst became inactive after only a short period of 1 day or less.

EXAMPLE 3

The process described in Example 1 above was repeated except that the solvent monitor used was tetraethylenepentamine instead of ethylenediamine. The products were analyzed and the conversion was determined to be about 100% with selectivity to the linear product, TREN, being about 70% while the cyclic product was only 30%.

EXAMPLE 4

The process described in Example 1 was repeated except that the polynitrile reactant was iminodiacetonitrile. The products were analyzed by gas-liquid chromatography and the conversion was determined to be about 100 percent with 85 percent selectivity to the linear product, diethylenetriamine.

EXAMPLE 5

The process described in Example 1 is repeated except that the polynitrile reactant is ethylenediaminetetraacetonitrile. The products are analyzed and the conversion of the polynitrile and the selectivity to the linear product, tetrakis(2-aminoethyl)ethylenediamine, are substantially the same values achieved in Example 4 above.

The above examples are given for illustrative purposes only and are not meant to be a limitation on the subject process nor the claims appended hereto.

We claim:

1. A process of converting polynitriles to non-cyclic, aliphatic compounds having a plurality of primary amino groups comprising, in a fixed-bed reactor maintained at a temperature of from about 50° C. to about 150° C. and having granular Raney cobalt packing therein, introducing into the reactor an aliphatic polynitrile having cyano groups directly separated by from 2 to 3 atoms in conjunction with at least about 5 weight percent based on the polynitrile of a liquid primary or secondary amine containing compound, contacting the polynitrile with the Raney cobalt in the presence of hydrogen pressure of from about 2000 to 10,000 psi for a time sufficient to produce non-cyclic, aliphatic compounds having a plurality of primary amino groups as the dominant product and recovering said aliphatic polyamines.

2. The process of claim 1 wherein said polynitrile in said reactor is maintained at a flow rate of from 0.02 to 10 gm of polynitrile per min-cm$^2$ and said polynitrile, amine, hydrogen and Raney cobalt are maintained in said reactor under trickle bed conditions.

3. The process of claim 1 wherein the hydrogen and amine are passed through the reactor concurrently with the polynitrile; that the hydrogen flow rate is from 100 to 3,000 scc/min-cm$^2$; the hydrogen pressure is at least about 2000 psi; and the total liquid flow rate is from 0.1 to 50 cc/min-cm$^2$.

4. The process of claim 2 wherein the hydrogen is passed through the reactor concurrently with the polynitrile; that the hydrogen flow rate is from 100 to 3,000 scc/min-cm$^2$; the hydrogen pressure is at least about 2000 psi; and the total liquid flow rate is from 0.1 to 50 cc/min-cm$^2$.

5. The process of claim 1 wherein the Raney cobalt has a particle size of from 0.025 to 0.5 inch mean diameter and is formed by removal of from 20 to 40% of the aluminum from an initial alloy composed of about 50 to 70 wt. % aluminum, about 30–50 wt. % cobalt, 0 to about 6 wt. % chromium and 0 to about 6 wt. % molybdenum.

6. The process of claim 2 wherein the Raney cobalt has a particle size of from 0.025 to 0.5 inch mean diameter and is formed by removal of from 20 to 40% of the aluminum from an initial alloy composed of about 50 to 70 wt. % aluminum, about 30–50 wt. % cobalt, 0 to about 6 wt. % chromium and 0 to about 6 wt. % molybdenum.

7. The process of claim 3 wherein the Raney cobalt has a particle size of from 0.025 to 0.5 inch mean diameter and is formed by removal of from 20 to 40% of the aluminum from an initial alloy composed of about 50 to 70 wt. % aluminum, about 30–50 wt. % cobalt, 0 to about 6 wt. % chromium and 0 to about 6 wt. % molybdenum.

8. The process of claim 1 wherein the reactor is maintained at a temperature of from about 70° C. to about 120° C.; the polynitrile is introduced into the reactor at a flow rate of from 0.05 to 2 gm/min-cm$^2$; the amine forms the solvent medium for the polynitrile solution; and the hydrogen pressure is from about 2000 to 5000 psig.

9. The process of claim 2 wherein the reactor is maintained at a temperature of from about 70° C. to about 120° C.; the polynitrile is introduced in the reactor at a flow rate of from 0.05 to 2 gm/min-cm$^2$; the amine forms the solvent medium for the polynitrile solution; and the hydrogen pressure is from about 2000 to 5000 psig.

10. The process of claim 1 wherein the polynitrile is nitrilotriacetonitrile and the major recovered product is tris(2-aminoethyl) amine.

11. The process of claim 2 wherein the polynitrile is nitrilotriacetonitrile and the major recovered product is tris(2-aminoethyl) amine.

12. The process of claim 6 wherein the polynitrile is nitrilotriacetonitrile and the major recovered product is tris(2-aminoethyl) amine.

13. The process of claim 9 wherein the polynitrile is nitrilotriacetonitrile and the major recovered product is tris(2-aminoethyl) amine.

14. The process of claim 1 wherein the polynitrile is iminodiacetonitrile and the major recovered product is diethylenetriamine.

15. The process of claim 2 wherein the polynitrile is iminodiacetonitrile and the major recovered product is diethylenetriamine.

16. The process of claim 6 wherein the polynitrile is iminodiacetonitrile and the major recovered product is diethylenetriamine.

17. The process of claim 9 wherein the polynitrile is iminodiacetonitrile and the major recovered product is diethylenetriamine.

18. The process of claim 1 wherein the polynitrile is ethylenediaminetetraacetonitrile and the major recovered product is tetrakis(2-aminoethyl) ethylenediamine.

19. The process of claim 2 wherein the polynitrile is ethylenediaminetetraacetonitrile and the major recovered product is tetrakis(2-aminoethyl) ethylenediamine.

20. The process of claim 6 wherein the polynitrile is ethylenediaminetetraacetonitrile and the major recovered product is tetrakis(2-aminoethyl) ethylenediamine.

21. The process of claim 9 wherein the polynitrile is ethylenediaminetetraacetonitrile and the major recovered product is tetrakis(2-aminoethyl) ethylenediamine.

22. The process of claim 1 wherein the granular Raney cobalt alloy is of a particle size of from about 0.05 to 0.4 inch mean diameter and contains up to 5 wt. percent chromium, the liquid amine is present in a molar excess to the polynitrile reactant and is selected from ethylenediamine and tetraethylenepentamine, the hydrogen pressure is from 2,500 to 4,000 psi, the polynitrile reactor flow rate is from 0.05 to 2 g of polynitrile/min-cm$^2$, the reactor temperature is maintained at from about 70° C. to 120° C. and the hydrogen, amine and polynitrile flow concurrently through the reactor.

23. The process of claim 2 wherein the granular Raney cobalt alloy is of a particle size of from about 0.05 to 0.4 inch mean diameter and contains up to 5 wt. percent chromium, the liquid amine is present in a molar excess to the polynitrile reactant and is selected from ethylenediamine and tetraethylenepentamine, the hydrogen pressure is from 2,500 to 4,000 psi, the polynitrile reactor flow rate is from 0.05 to 2 g of polynitrile/min-cm$^2$, the reactor temperature is maintained at from about 70° C. to 120° C. and the hydrogen, amine and polynitrile flow concurrently through the reactor.

24. The process of claim 6 wherein the granular Raney cobalt alloy is of a particle size of from about 0.05 to 0.4 inch mean diameter and contains up to 5 wt. percent chromium, the liquid amine is present in a molar excess to the polynitrile reactant and is selected from ethylenediamine and tetraethylenepentamine, the hydrogen pressure is from 2,500 to 4,000 psi, the polynitrile reactor flow rate is from 0.05 to 2 g of polynitrile/min-cm$^2$, the reactor temperature is maintained at from about 70° C. to 120° C. and the hydrogen, amine and polynitrile flow concurrently through the reactor.

25. The process of claim 9 wherein the granular Raney cobalt alloy is of a particle size of from about 0.05 to 0.4 inch mean diameter and contains up to 5 wt. percent chromium, the liquid amine is present in a molar excess to the polynitrile reactant and is selected from ethylenediamine and tetraethylenepentamine, the hydrogen pressure is from 2,500 to 4,000 psi, the polynitrile reactor flow rate is from 0.05 to 2 g of polynitrile/min-cm$^2$, the reactor temperature is maintained at from about 70° C. to 120° C. and the hydrogen, amine and polynitrile flow concurrently through the reactor.

* * * * *